(12) United States Patent
Bergeron et al.

(10) Patent No.: US 8,236,360 B2
(45) Date of Patent: Aug. 7, 2012

(54) SUPERCRITICAL $CO_2$ LIQUORICE EXTRACT AND PRODUCTS MADE THERE FROM

(75) Inventors: Chantal Bergeron, Kennebunkport, ME (US); Stefan Gafner, Kennebunkport, ME (US)

(73) Assignee: Tom's of Maine, Inc., Kennebunkport, ME (US)

( * ) Notice: Subject to any disclaimer, the term of this patent is extended or adjusted under 35 U.S.C. 154(b) by 0 days.

(21) Appl. No.: 11/799,524

(22) Filed: May 2, 2007

(65) Prior Publication Data

US 2008/0274179 A1    Nov. 6, 2008

(51) Int. Cl.
*A61K 36/48* (2006.01)
(52) U.S. Cl. ........................................................ 424/757
(58) Field of Classification Search .................. None
See application file for complete search history.

(56) References Cited

U.S. PATENT DOCUMENTS

| | | | |
|---|---|---|---|
| 1,849,569 A | 5/1932 | Condorelli et al. | |
| 3,066,072 A * | 11/1962 | Gottfried et al. | 424/725 |
| 4,176,228 A * | 11/1979 | Hartung | 536/18.1 |
| 4,545,979 A | 10/1985 | Ambike et al. | |
| 4,639,466 A | 1/1987 | Huang et al. | |
| 5,496,541 A * | 3/1996 | Cutler | 424/49 |
| 5,660,870 A | 8/1997 | Schantz | |
| 6,280,780 B1 | 8/2001 | Degady | |
| 6,319,523 B1 | 11/2001 | Zhou | |
| 6,479,043 B1 | 11/2002 | Tietjen et al. | |
| 6,586,018 B1 | 7/2003 | Fasano | |
| 6,861,062 B2 | 3/2005 | Silva et al. | |
| 6,979,471 B1 * | 12/2005 | Khanuja et al. | 424/757 |
| 7,179,454 B2 | 2/2007 | Lucas | |
| 7,201,930 B2 * | 4/2007 | Haley | 424/757 |
| 7,288,270 B1 * | 10/2007 | Sekharam et al. | 424/725 |
| 7,303,762 B2 * | 12/2007 | New | 424/463 |
| 7,524,975 B2 | 4/2009 | Mae et al. | |
| 2002/0037332 A1 * | 3/2002 | Cohen | 424/757 |
| 2003/0203054 A1 * | 10/2003 | Selzer et al. | 424/732 |
| 2003/0228379 A1 * | 12/2003 | Shi et al. | 424/725 |
| 2004/0028736 A1 * | 2/2004 | New | 424/471 |
| 2004/0115138 A1 * | 6/2004 | Healy et al. | 424/49 |
| 2004/0161524 A1 * | 8/2004 | Sakai et al. | 426/655 |
| 2005/0048007 A1 * | 3/2005 | Ruggles | 424/58 |
| 2005/0118288 A1 | 6/2005 | Yamashita et al. | |
| 2005/0118289 A1 | 6/2005 | Ikehara et al. | |
| 2005/0119156 A1 | 6/2005 | Turin | |
| 2006/0052438 A1 * | 3/2006 | Ho et al. | 514/453 |
| 2006/0269494 A1 | 11/2006 | Gupta | |
| 2007/0116652 A1 * | 5/2007 | Kamath et al. | 424/58 |

FOREIGN PATENT DOCUMENTS

| | | |
|---|---|---|
| CN | 1272501 | 11/2000 |
| CN | 1359905 | 7/2002 |
| CN | 1803789 | 7/2006 |
| EP | 1057825 | 12/2000 |
| FR | 2735477 | 1/1997 |
| GB | 457349 | 11/1936 |
| JP | 55039671 A * | 3/1980 |
| JP | 55039671 A | 3/1980 |
| JP | 56015654 A * | 2/1981 |
| JP | 56015654 A | 2/1981 |
| JP | 60178815 | 2/1981 |
| JP | 02233795 A * | 9/1990 |
| KR | 2003090188 | 5/2002 |
| KR | 2005/041390 | 5/2005 |
| KR | 0041390 | * 10/2005 |
| KR | 2006008509 | 1/2006 |
| RU | 2130733 | 5/1999 |
| WO | WO 02/066041 | 8/2002 |

OTHER PUBLICATIONS

Raventos et al (Food Science Tech. Int. (2002), vol. 8 (5), pp. 269-284).*
Hatano et al. The Phenolic constituents of licorice, VIII. Structures of glicophenone and glicoisoflavanone, and effects of licorice phenolics on methicilin-resistant *Staphylococcus aureus*, Biological and Pharmaceutical Bulletin, 2000, vol. 48, No. 9, pp. 1286-1292.*
Hatano et al, Effects of tannins and related polyphenols on methicillin-resistant *Staphylococcus aureus*, (Phytochemistry, vol. 66, 2005, pp. 2047-2055).*
Fukai et al., "Anti-*Helicobacter pylori* flavonoids from licorice extract", (Life Sciences, vol. 71, 2002, pp. 1449-1463).*
"Deglycyrrhizinated licorice" from Wikipedia, as cited in U.S. Appl. No. 12/150,920) on Oct. 18, 2010.
Bodet et al., "A Licorice extract reduces lipopolyusaccharide-induced proinflammatory cytokine secretion by macrophages and whole blood," J. Periodontol., 79(9):1752-1761, 2008.
3rd Party Observations in corresponding EP Application No. 08767466.9 including references with English translation dated Jun. 6, 2011.
Fu et al., "Supercritical Fluid Extraction of Seed Oil from Chinese Licorice," S. Afr. J. Chem. 60, 2007.
Fuhrman et al., "Licorice Extract and its major polyphenol glabridin porotect low-density lipoprotein against lipid peroxidation," Am. J. Clin. Nutr., 66:267-275, 1995.
Fukai et al., "Anti-*Helicobacter pylori* flavonoids from licorice extract," Life Sciences 71: 1449-1463, 2002.

(Continued)

*Primary Examiner* — Christopher R. Tate
*Assistant Examiner* — Deborah A. Davis
(74) *Attorney, Agent, or Firm* — Nikhil A. Heble (57) ABSTRACT

The present invention provides, in one aspect, to products made from a novel and non-obvious supercritical $CO_2$ extract of the roots of *Glycyrrhiza* sp., effective as an anti-inflammatory, anti-bacterial, anti-fungal and anti-adherent agent, including, but not limited to, products for oral care and body care.

20 Claims, 2 Drawing Sheets

OTHER PUBLICATIONS

Goultschin et al., "Effect of glycyrrhizin-containing toothpaste on dental plaque reduction and gingival health in humans," J. Clin. Period. 18:210-212, 1991.

Krausse et al., "In vitro anti-*Helicobacter pylori* activity of extractum liqquiritiae, glycyrrhizin and its metabolites," J. Antimicrobial. Chemotherapy, 54:243-246, 2004.

Mae et al., "A Licorice Ethanolic Extract with Peroxisome Proliferator-Activated Receptor-y Ligand-Binding Activity Affects Diabetes . . .," J. Nutrition, 133:3369-3377, 2003.

Toshio et al., "Antimicrobial activity of licorice flavonoids against methicillin-resistant *Staphylococcus aureus*," Fitoterapia 73: 536-539, 2002.

Goultschin, et al., J. Clin. Periodontol. 18:210-212, 1991.

Krausse, et al., J. Antimicrobial Chemotherapy, 54:243-246, 2004.

Mae, et al., J. Nutrition, 133:3369-3377, 2003.

Fuhrman, et al., Am. J. Clin. Nutr., 66:267-275, 1997.

\* cited by examiner

SUPERCRITICAL CO$_2$ LIQUORICE EXTRACT AND PRODUCTS MADE THERE FROM

BACKGROUND

Extracts from the root of plants of the genus *Glycyrrhiza* (*Glycyrrhiza* sp.), are used for flavorings, the extract imparting the flavor of licorice (liquorice), among other purposes. Current extraction methods use a hot water extraction method. This method preferentially isolates hydrophilic components of the plant root. The major single component isolated with the prior art extraction methods is glycyrrhizic acid. Glycyrrhizic acid is used predominately as a sweetener and a flavoring. Prior art extraction methods remove little or none of the hydrophobic or lipophilic components of the plant root.

Other prior art methods use organic solvents in the extraction process. These processes remove more of the lipophilic components of the plant root but have major environmental concerns connected with the use of the organic solvents. Furthermore, both of the prior art extraction processes (hot water and organic solvent) have significant problems in terms of, for example, waste generation and elimination. Organic solvent extracts have, by their very nature, the problem of spent organics to dispose of or recycle. Hot water extraction processes are preferred at extracting hydrophilic compounds are not effective in extracting lipophilic compounds. Additionally, the spent water must be treated before being put back into the water supply of the environment.

Various components of extracts of *Glycyrrhiza* sp. have been shown to have anti-inflammatory, antibacterial and anti-adherent effects. However, the effects seen by prior art extracts have been inconsistent. For example, in one study it was reported that incorporation of 0.25-0.5% of glycyrrhizic acid (a major component of licorice extracts made by prior art extraction methods) was ineffective in the removal or prevention of plaque build up (Goultschin, et al., J. Clin. Periodontol. 18:210-212, 1991).

Therefore, what is needed is a method for the extraction of the root of *Glycyrrhiza* sp. that produces less waste and causes a lesser impact on the environment than prior art extracts while at the same time producing an extract that is more effective in providing anti-inflammatory, antibacterial and anti-adherent properties by isolating a greater percentage of the total available lipophilic components of the plant root and, in particular, a greater total percentage of the available prenylated flavonoids of the plant root.

SUMMARY OF THE INVENTION

The present invention provides, in one aspect, novel and non-obvious methods of producing extracts from the roots of *Glycyrrhiza* sp. In one embodiment, the method of extraction of the present invention comprises utilizing a supercritical CO$_2$ extraction process. Details of the process of the present invention are given below in the Description of the Preferred Embodiments. The methods of the present invention solve the problems of the prior art extraction methods by greatly reducing or eliminating the need for organic solvents during the extraction process and providing an extract that is rich in prenylated flavonoids (e.g., isoflavans, isoflavonol, flavanone, isoflavone) while also being virtually void or void of glycyrrhizic acid (e.g., with no detectable glycyrrhizic acid). The methods of the present invention also extract lipophilic components while extracting very little of the hydrophilic components. The method of the present invention also greatly reduces or eliminates the production of a waste water stream as a result of the extraction process.

The present invention further relates to the extracts made from the extraction processes of the present invention. In one embodiment, the extract of the present invention comprises an extract from *G. uralensis* comprising predominately licoricidin and 5-O-methyllicoricidin as the lipophilic components. No detectable glycyrrhizic acid, a hydrophilic component of the plant root, is recovered with the extraction process of the present invention. Both, licoricidin and 5-O-methyllicoricidin are prenylated isoflavans, a particular type of flavonoids. For licoricidin, the molecular weight is m/z=424. For 5-O-methyllicoricidin: molecular weight m/z=438; UV (MeOH): λmax=283 nm. In one embodiment, the extract of the present invention is isolated without using ethanol as a modifier during the extraction process. In this embodiment, the concentration ranges of licoricidin and 5-O-methyllicoricidin are approximately 0.5-5.0% for both. In another embodiment, the extract of the present invention is produced using ethanol as a modifier during the extraction process. In this embodiment, the concentration ranges of licoricidin and 5-O-methyllicoricidin are approximately 2.0-10.0% for licoricidin and 1.0-5.0% for 5-O-methyllicoricidin. In yet another embodiment, the concentration of glycyrrhizic acid in the extracts is less than 0.10%. In yet another embodiment, the concentration of glycyrrhizic acid in the extracts is less than 0.01% or 0.001%. Furthermore, the supercritical CO$_2$ extracts of the present invention also comprises significant amounts of fatty acids (plamitic and linoleic acids, in particular, for example).

Other species of *Glycyrrhiza* provide extracts wherein the predominant lipophilic components are prenylated flavonoids although the exact prenylated flavonoids may differ. For example, an extract of *G. glabra* made by the extraction process of the present invention would have as the major prenylated flavonoids, glabridin, methylglabridin and glabrol.

When ethanol is used as a modifier in the extraction process of the present invention, the ethanol is at a concentration of between approximately 2.0 and 10%. In a preferred embodiment, the ethanol modifier is between approximately 4.0 and 6.0%. The use of ethanol is not necessary to produce the extracts of the present invention. Ethanol helps to extract highest amount of compounds which have less lipophilic properties than using CO$_2$ alone.

The present invention also relates to products that are made from said extracts. Although the present invention is not limited to any particular use for the extract of the present invention, in a preferred embodiment, the extract is used in an oral care product. Examples of suitable oral care products in which the extract of the present invention can be used include, but are not limited to, dentifrices (e.g., toothpaste, toothpaste gels, toothpowders, denture cleaning agents and compounds, mouthwashes and mouth rinses, toothpicks, dental floss, chewing gums, pastilles, lozenges, dissolvable tablets, chewable tablets, etc.). Additionally, the extracts of the present invention may be used in body care products such as, but not limited to, skin creams, sun screen compositions, soaps, baby care products, shaving products, deodorant, etc.

DESCRIPTION OF THE PREFERRED EMBODIMENTS

The present invention relates to extracts from *Glycyrrhiza* sp. that have less environmental impact than prior art extraction methods and that extract a greater percentage of the lipophilic components while extracting fewer hydrophilic components than the prior art methods. The present invention also relates to uses for the extracts of the present invention. In another aspect, the present invention relates to an extraction process of *Glycyrrhiza* sp. that utilizes a supercritical $CO_2$ extraction process.

Extracts may be made from the root of many different species of legume-like plants from the genus *Glycyrrhiza* and more particularly from the species *Glycyrrhiza uralensis*. The plants are native to southern Europe and parts of Asia. *G. uralensis* is used extensively in traditional Chinese medicine. Still, the present invention is not limited to any specific plant source. Other known species of *Glycyrrhiza* from which extracts my be made thorough the processes of the present invention include, but are not limited to, *Glycyrrhiza acanthocarpa, Glycyrrhiza aspera, Glycyrrhiza astragalina, Glycyrrhiza bucharica, Glycyrrhiza echinata, Glycyrrhiza eglandulosa, Glycyrrhiza foetida, Glycyrrhiza foetidissima, Glycyrrhiza glabra, Glycyrrhiza gontscharovii, Glycyrrhiza iconica, Glycyrrhiza korshinskyi, Glycyrrhiza lepidota, Glycyrrhiza pallidiflora, Glycyrrhiza squamulosa, Glycyrrhiza triphylla, Glycyrrhiza uralensis* and *Glycyrrhiza yunnanensis*.

Supercritical carbon dioxide refers to carbon dioxide with some unique properties. Carbon dioxide usually behaves as a gas in air or as a solid as dry ice. If the temperature and pressure are both increased, it can adopt properties midway between a gas and a liquid. It behaves like a supercritical fluid above its critical temperature (31.1 degrees Celsius) and pressure (73 atm=73.96 bar), expanding to fill its container like a gas, but with a density like that of a liquid. The actual temperature necessary to create a supercritical $CO_2$ depends on the pressure and vice versa. For example, the higher the pressure, the lower the temperature necessary to reach the supercritical state. Likewise, the higher the temperature, the lower the pressure necessary to reach the supercritical state.

Although supercritical $CO_2$ has been used in some instances as an extractant for other substances, it has not, to the best of our knowledge, been used as an extractant for the extraction of *Glycyrrhiza* sp root especially wherein the resulting extract comprised predominately prenylated flavonoids (prenylated isoflavans) and specifically licoricidin and 5-O-methyllicoricidin from *G. uralensis* (and, similarly, the prenylated flavonoids glabridin, methylglabridin and glabrol from *G. glabra*) and was essentially free or void of glycyrrhizic acid. It was only through the empirical experimentation that the methods and compositions of the present invention were conceived and reduced to practice. There were no market pressures or other market considerations that would have led one practiced in the art to identify or develop the components of the present invention, modify the components as necessary to conceive and practice the present invention and to conceive and produce the products of present invention. It was only after the conceptual reduction to practice of the present invention that any market value was recognized.

Some of the environmental benefits of using supercritical $CO_2$ are as follows. First, the $CO_2$ that is used in the process is essentially unchanged and can be reused repeatably. Second, there is virtually no waste stream, i.e., no spent solvent, volatile organic compounds, contaminated waste water, etc., to deal with. Thus, the extract of the present invention is environmentally more sound than the extracts of the prior art methods.

The extracts of the present invention are unlike prior art extracts of *Glycyrrhiza* sp. The extracts of the present invention are high in the compounds known as prenylated flavonoids (e.g., licoricidin and 5-O-methyllicoricidin). Both of these compounds have anti-inflammatory, antibacterial, anti-adherent and anti-fungal effects and licoricidin has significant antibacterial activity. For example, the extract of the present invention has been shown to have significant antibacterial activity against gram-positive bacteria such as *Staphylococcus aureus* and *Streptocuccus mutans* and antifungal activity against *Aspergillus niger*. Thus, it can be seen that these compounds can excel in their ability to act as anti-inflammatory, antibacterial and as antifungal agents (See, Experimental section, below).

Additionally, the extracts of the present invention are void or virtually void of glycyrrhizic acid when examined by high pressure liquid chromatography (HPLC) (see, Experimental Section, below). Glycyrrhizic acid has been used a sweetener and flavor in the prior art and is not needed in the compositions of the present invention.

As mentioned above, the extract produced by the process of the present invention can be used in many products including oral care products and body care products for their anti-inflammatory, antibacterial, anti-adherent and antifungal properties. Below, we describe some of the products suitable for use with the extract of the present invention.

Oral Compositions

Floss

The *Glycyrrhiza* sp root (i.e., licorice extract) of the present invention may be formulated in a dental floss. For example, the extracts of the present invention may be impregnated within dental floss so that it comes into contact with the user's teeth during flossing. Concentrations of the extract of the present invention when used in a dental floss composition are between 0.1-5.0% of the wax mixture used in coating the floss material. Preferred concentrations are between 0.5 and 3.0% of the wax mixture used in coating the floss material. Dental floss may be used to ensure that the extracts of the present invention come into contact with the surfaces of the teeth that face each other and are hard to reach by some of the other means described.

In certain embodiments of the present invention, said dental floss is made as discussed below. One skilled in the art will realize that there are other methods and compositions for the manufacture of dental floss that are compatible with the licorice-based composition of the present invention.

The meaning of the words, "dental floss(es)," shall be herein understood to include both dental flosses and dental tapes as well as any other similar article. Moreover, the dental flosses and tapes used in the present invention may include any suitable or commercially available dental floss or tape. These flosses and tapes can be fabricated from either natural or synthetic sources examples of which include, but are not limited to, filaments or yarns of high and normal tenacity polymers, GoreTex™, nylons, polyolefins, polyethylenes, polypropylenes, fluorocarbon compounds, polytetrafluoroethylenes, rayons, dacrons, acrylics, acetate polymers, and other plastics alone or in combination. Natural substances may include, but are not limited to, cotton, wool, silk, linen, hemp, soy and other staple fibers alone or in combination. Blends of synthetic-natural fibers can also be used. However, synthetic filaments tend to fray less than natural fibers.

The tensile strength of floss must be evenly distributed along their length. This is the key with fibers—they will break at their weakest point, so even keeled tensile strength is the key. Thus, the dental floss of the present invention is related to fibers with high tensile strength while still being usable for cleaning between teeth. The denier of a floss or floss fiber measures it's weight and also to tensile strength. Denier is defined as the weight of 9,000 meters of uncoated floss in grams. There is a direct correlation between the numerical value of the denier and the thickness of the strand of floss: if this value increases, the thickness of the strand also increases. Thus, generally, the higher the denier, the higher the tensile strength, all else being equal. In one embodiment of the present invention, the denier of round floss is between about 750-950 and for flat floss it is between about 950 and 1150.

The length, diameter, structure or design of the floss itself is also not limited to any specific size, shape, arrangement or configuration and, thus, can be fabricated to suite any specific intention. It can, for example, be composed of a plurality of individual filaments that have been formed together to give a larger thread having a sufficiently small diameter to permit insertion between the teeth. It can also comprise a composite multifilament yarn bonded to an extruded monofilament or to another multifilament yarn. A single circular, square or rectangular shaped monofilament thread is also useful. Other suitable variations are also well known in the art and as such are also useable in the invention disclosed herein.

Binders, for example, are used in the invention disclosed herein to bind or otherwise attach to a dental floss the ingredients herein specified by this disclosure. They also provide the ability to alter the frictional characteristics of dental floss as well as help bind together the individual filaments comprising the floss itself. Moreover, the varieties used herein are not restricted to any specific types or compositions and are thus, given great freedom in their formulations, structures or make-ups. Examples of some suitable binders may therefore include, but are not limited to, natural waxes from plants (e.g., carnauba wax, soy wax and jojoba wax) as well as other water soluble or non-water soluble wax or wax-like compounds or water soluble or non-water soluble polymers, soaps, gums, resins (e.g., myrrh and propolis) and other substances known in the art.

Flosses may also make use of, for example, one or more solubilizing agents. Their function, as such, will be to aid in dissociation. Suitable solubilizing agents may therefore include, but are not limited to, filtered water, reverse osmosis water, distilled water and deionized water, alone or in combination. However, deionized water has been found preferable to the others.

Flosses may also utilize, for example, one or more flavoring agents. These preferably comprise oils or extracts derived from plants and fruits such as citrus oils, fruit essences, mint, peppermint oil, spearmint oil, clove oil, oil of wintergreen, anise, sassafras, sage, eucalyptus, marjoram, cinnamon, lemon, orange, banana, cherry, fennel, apple, pineapple, grape, strawberry and blueberry. Those skilled in the art will recognize that such natural flavoring agents may be used independently or combined in any sensorially acceptable blend. All such flavors and flavor blends are contemplated by the present invention.

To foster greater consumer appeal, flosses may also contain, for example, one or more natural sweetening agents. These may include, but are not limited to, xylitol, glycerol, sorbitol, maltitol, erythritol, sucrose, lactose, dextrose, maltose, dextrin, fructose, galactose and the like.

Fluorides have in the past been found to help prevent the incidence of carious lesions or caries. Caries are caused when teeth demineralize at a rate faster than they remineralize and most demineralization is caused by acid producing dental plaques. Remineralization, however, is promoted by calcium and phosphate, the chief remineralizing agents found also in saliva. Fluoride based compounds, therefore, provide protection from carious lesions or caries by acting as a catalyst to speed the precipitation of calcium phosphate, in the form of a hydroxy apatite, onto or into teeth. However, this is not fluoride's only role. It is also able to inhibit the activity of some bacterial enzymes and their acid producing processes, and at extremely high concentrations it can also kill certain plaque bacteria. Even more important, it tends to become incorporated into the apatite, as a fluoridated hydroxy apatite or "fluorapatite," creating a mineral that is appreciably less dissolvable by acid.

Hence, flosses may contain, for example, one or more fluoride based compounds. These compounds may also be slightly soluble in water or may be fully water soluble. They are, however, foremost characterized by their ability to release fluoride ions in water and their freedom from undesired reactions with the floss's other compounds. Among these materials are numerous fluoride-based compounds which can comprise inorganic fluoride salts such as soluble alkali metal, alkaline earth metal salts, and others. When a fluoride compound is employed, the amount used is dependent to a large extent upon the type of fluorine compound, its solubility, and the final formulation and structure selected. As such, substantial leeway is given to the quantities or amounts used as long as normal formulation and pharmaceutical safeguards are observed. Consequently, whenever fluoride based compounds are used within the formulations listed below they should amount to no more than 0.30 percent (w/w). However, it has been found that setting the maximum range at 0.24 percent (w/w) is preferable with 0.22 to 0.24 percent (w/w) being the best overall range to use.

Dentifrice

The licorice supercritical $CO_2$ extracts (*Glycyrrhiza* sp root extract) of the present invention may also be used with toothpastes, tooth gels and tooth powders. In one embodiment of the present invention, the concentration of the extract of the present invention used in dentifrices ranges from about 0.002-2.0%. In a preferred concentration the range is between 0.02-1.0%.

Compositions in the form of toothpastes, gels, liquid gels, denture cleansing liquids and pastes, and the like, will generally comprise a binder or thickening agent. Binders suitable for use herein include carrageenan (preferred) and/or natural gums such as gum karaya, xanthan gum (preferred), gum arabic (preferred) and gum tragacanth can also be used, as well as other agents known in the art. Colloidal magnesium aluminium silicate or finely divided hydrated silica can be used as part of the thickening agent to further improve texture. Binders/thickening agents can be used in an amount from about 0.1% to about 15.0%, preferably from about 1.0 to about 12% by weight of the total composition. The actives are fluoride and potassium nitrate, their level are described in their respective FDA monographs for anti-cavity and sensitivity. Active for gingivitis are still pending the finalization of the monograph. The abrasives are calcium carbonate, baking soda or hydrated silica.

Such compositions will typically comprise one or more sweeteners and flavorings. Examples of suitable sweeteners and flavorings for use in dentifrices are discussed above. pH balancing agents (e.g., citric acid, NaOH) as well as, surfactants (e.g., sodium lauryl sulfate), preservatives (e.g., benzoic acid, sorbic acid) stabilizers, etc., are also often used in dentifrice compositions, examples of which are also provided above. The compositions of the present invention may include botanicals as well.

In addition to the incorporation of licorice extract of the present invention, there may also be included in the dentifrice minor amounts, e.g., 0.01 to 2% by weight of other natural ingredients such as antioxidants, preservatives, pH adjusting agents, desensitizing agents, stabilizing agents, gelling agents, flavors, etc. A preferred gelling or binding agent is one or more of carrageenan or xanthan gum. Preferred flavorings are natural flavorings such as peppermint, spearmint, apricot and cinnamon, etc. For sensitive teeth, the formulation may contain an agent for relieving pain in people with sensitive teeth. A preferred ingredient for this purpose is potassium nitrate. Dispersing agents may be used in the present invention. Preferred dispersants are sodium lauryl sulfate or saponin containing plant extracts.

It is also desirable to include one or more humectants (moisture retaining agent) material in the toothpaste to keep the composition from hardening upon exposure to air. Preferred humectants are glycerin and sorbitol. Certain humectants can also impart a desirable sweetness to toothpaste compositions. Liquid dentifrice and mouthwashes can also contain a quantity of humectants. Suitable humectants are well known in the art. When present, humectants generally represent from about 10% to about 70%, by weight of the compositions of the invention.

Toothpowders may make use of many of the same ingredients as toothpastes except that they must be mixed in a dried state (i.e., dry milled) or mixed as a liquid composition and then dried via, for example, various known spray drying techniques. Spray drying is described as when a liquid form of a composition is sprayed as a mist into a hot, dry chamber wherein the aqueous portion of the mist is evaporated by the dry heat of the chamber leaving only the dry constituents of the composition in a powdered form. The powdered form of the composition has a moisture content of between about 0.1% to 5%. Toothpowders then rehydrate upon use either by the addition of water (e.g., with water applied by the user) at the time of use or by the user's saliva.

Dissolvable Tablets

Another aspect of the present invention is dissolvable denture cleaning tablet comprising the *Glycyrrhiza* sp. supercritical $CO_2$ extract of the present invention. Such tablets may be solid, layered, have a liquid filled center, etc. The tablet should dissolve completely or nearly completely in an aqueous solution in less than about one hour and, preferably, in less than about 15 minutes. The tablet may be effervescent but need not be.

Water-soluble, denture cleanser tablets are made by first preparing and drying a granulation of ingredients using a suitable binder in an, for example, anhydrous alcohol solution. The resulting granular mixture is then dried to a moisture content of 0.4% or less, screened, and then thoroughly blended with the desired active ingredients along with binders, fillers, extenders, dyes, flavors, lubricants and the like in a suitable blending apparatus. The final blends are fed into a punch and die tableting press where it is compacted into tablets. Thereafter the tablets so formed are released and packaged.

Mouthwash and Mouthrinse

Typically, the mouthwashes and rinses of the present invention comprise the *Glycyrrhiza* sp. supercritical $CO_2$ extract of the present invention in, for example, a water/glycerin solution and may additionally comprise one or more of flavor, humectant, sweetener, emulsifier (e.g., poloxamer) and colorant. Mouthwashes can include glycerin at a level of from 0 to 60%, preferably from 0 to 30% by weight. The pH value of such mouthwash preparations is generally from about 3.5 to about 8.0 and preferably from about 4.0 to about 7.5. A pH greater than 8.7 would result in an unpleasant mouth feel. The oral liquid preparations may also contain surface active agents, i.e., surfactants, in amounts up to about 5.0% and more preferably between about 0.5-2.0%; and fluoride-providing compounds in amounts up to about 2.0% by weight of the preparation and more preferably about 0.0442% for sodium fluoride or 0.025% of the fluoride ion.

The mouthwashes and mouth rinses of the present invention may also comprise one or more alcohols. For example, ethanol.

Pastilles, Lozenges and Chewing Gum

The chewing gum compositions that comprises the *Glycyrrhiza* sp. supercritical $CO_2$ extract of the present invention may be in the form of a conventional chewing gum or any other product form which is suitable for chewing. Suitable physical forms include sticks, squares and dragees (i.e., sugar coated gum; e.g., Chiclets™). The chewing gum may also have a liquid-filled center wherein the liquid center contains the licorice-based compositions (See, e.g., U.S. Pat. No. 6,280,780). The chewing gum may also be a digestible or dissolvable gum suitable for chewing. A chewing gum is typically retained in the oral cavity for a time sufficient to allow ingredients released to contact substantially all of the dental surfaces and/or oral tissues for purposes of oral activity.

The term "carrier materials" as used herein means any safe and effective additional chewing gum components used in the chewing gum compositions of the present invention. Such materials include elastomers, resins, plasticisers, fats, solvents, waxes, emulsifiers, softeners, bulking agents, sweeteners, absorbents, orally active metallic ions, cationic material, fluoride ion sources, additional anticalculus agents, antimicrobial agents, buffers, whitening agents, alkali metal bicarbonate salts, thickening materials, humectants, water, surfactants, titanium dioxide, flavoring agents, xylitol, coloring agents and mixtures thereof.

The chewing gum of the present invention is manufactured by methods known in the art. For example, the gum base is heated to 45° C. to soften. The mixer vessel is maintained at 45° C. during entire mixing process and additives as described herein as well as the extract of the present invention are added and mixed to homogeneity. Then the gum mixture is formed into sticks, squares, etc., wrapped and cooled. If desired, the gum is coated in a sugar or sugar-free candy coating.

The licorice composition may also be used in lozenge and pastille compositions. The carrier for the lozenges and pastilles is conveniently a sugar, such as glucose, lactose or sucrose, or a substantially non-cariogenic material, for example mannitol, xylitol, maltitol, erythritol or sorbitol.

In addition to the active ingredient and the carrier, the lozenges preferably contain one or more binders, such as gelatin (a vegetal gum, e.g., Arabic gum, is preferred) or liquid glucose BPC 1963, which in total may conveniently be present in an amount of from about 0.5 to 10% weight of the lozenge. A preferred range is from about 1 to 5% by weight.

The lozenges may additionally contain a lubricant, such as stearic acid or a stearate such as magnesium stearate to facilitate manufacture of the lozenge. When one or more lubricants are present, the total content thereof in the lozenge is preferably from 0.1 to 5% by weight.

The lozenges may be prepared by conventional lozenge making procedures, for example by admixing the 1,3-bis(2-carboxychromon-5-yloxy)-2-hydroxypropane or salt thereof with the adjuvant, diluent or carrier and compressing the mixture. In a preferred procedure, the bis-chromone and the adjuvant, diluent or carrier are desirably first granulated together before being compressed into the lozenge. The granulation step is preferably a wet granulation step, and a lubricant is desirably added immediately before the compression step.

Pastilles (sometimes known as jujubes or soft lozenge) are a hard, jelly-like preparation made from a mixture of glycerin, gelatin (or other natural gelifiant) and water, to which the extract of the present invention is incorporated. Flavor may be added too. The glyco-gelatin base may be melted by gentle heating and any ingredients added. The warmed base is then poured into moulds and allowed to set. For example, See, http://www.rpsgb.org.uk/pdfs/mussheet04.pdf.

Body Care Products

Typical body care products include, for example, body lotions, skin creams, soaps, hair care products, sun screens, anti-inflammatory topical agents, depilatory compositions, shaving products, deodorant, baby care, etc. Body care products are products used on the external body (e.g., skin, hair, etc.) as, usually, topical treatments.

One practiced in the art knows how to formulate such body care products. For example, U.S. Pat. No. 6,861,062 to Silva, et al., (and incorporated herein by reference) discloses exemplary formulations and methods for making skin creams. Herbal compositions for skin care products are also known in the art (see, e.g., U.S. Pat. No. 6,586,018 to Fasano, which is incorporated herein by reference) discloses exemplary formulations and methods of manufacture.

Compositions and methods of producing shaving products are also known in the art. For example, U.S. Pat. No. 7,179,454 to Lucas, which is herein incorporated by reference, discloses several exemplary formulations and methods of manufacture. U.S. Pat. No. 6,479,043 to Tietjen, et al., (incorporated herein by reference) discloses exemplary formulations and methods of manufacture for depilatory agents.

Likewise, formulations and methods for the production of soaps, sun screen lotions and anti-inflammatory topical treatments are also known in the art.

Body care products of the present invention, in one embodiment, comprise an extract of the root of the plant *Glycyrrhiza* sp., comprising an essentially glycyrrhizic acid free extract wherein the major components of the extract are prenylated flavonoids and wherein the root was extracted by a supercritical $CO_2$ extraction process.

In another embodiment, the extract is from *Glycyrrhiza uralensis* and the major components of the extract are licoricidin and 5-O-methyllicoricidin.

In another embodiment, the extract is from extract is from *Glycyrrhiza glabra* and the major component of the extract is glabridin.

For example, a deodorant of the present invention, in one embodiment, comprises an extract of the present invention in combination with an antioxidant compound, preferably with an ingredient from the group of tocopherol and its derivatives, butyl hydroxyanisole (BHA), butyl hydroxytoluene (BHT), erythorbic acid, propyl gallate, sodium erythorbate, tertiary butyl hydroquinone (TBHQ), and rosemary extract, more preferably with ascorbic acid and salts thereof. Further, the deodorant may comprises certain metal salts of an unsaturated hydroxy carboxylic acid, preferably zinc ricinoleate. in a preferred embodiment, the extract of the present invention is at a concentration of about 0.01 to 5.0% and in a more preferred embodiment, from about 0.05 to 2.0%.

For body lotions, skin creams, soaps, hair care products, sun screens, anti-inflammatory topical agents, depilatory compositions, shaving products, baby care products the concentration of the extracts of the present invention are at a concentration of about 0.01-2% and more preferably 0.1-1%.

EXPERIMENTAL

Extraction Process: The licorice extract used in the following examples and in the manufacture of dentifrices of the present invention was made with a novel and non-obvious supercritical $CO_2$ extraction process. The extraction process of the present invention, in one embodiment, was as follows. The root of *Glycyrrhiza uralensis* was cut, ground and powdered to create a raw material. The raw material was put into an extraction chamber (the extractor). The extraction chamber was fed with liquid $CO_2$. The liquid $CO_2$, brought from the working/storage tank, was cooled and pumped into the extraction chamber at 300 bar, 50° C. with the 5% addition of 96% ethanol. The $CO_2$ extract was then metered through an evaporator and flowed into a separation tank.

Under supercritical conditions established in the extractor, $CO_2$ has solvent properties for lipophilic ingredients whereas $CO_2$ in the gas phase is without solvent power under the conditions in the separator (60 bar, 30° C.). Thus the extract was precipitated and the gas was regenerated in the separation tank. The $CO_2$ was then liquefied by passing through a condenser and recycled to the working tank.

Comparison of the Supercritical $CO_2$ Licorice Extract of the Present Invention with the Extracts Made by Prior Art Methods.

Broth microdilution minimum inhibitory concentration: For anaerobes, 190 µL of sterile, pre-reduced Wilkins Chalgren (WC) anaerobe broth with 0.075% cysteine were added to the first well of the test series in a 96 well plate, followed by 100 µL in each of four additional test wells. Ten µL of filter-sterilized stock solution of licorice $CO_2$ extract, prepared at 40 mg/mL in ethanol, was added to the first well of the series. Contents of the first well were mixed thoroughly and serially diluted (1:1) with the remaining four wells in the series; 100 µL were discarded from the final well in the series. Suspensions of *Porphyromanas gingivalis* ATCC 33277 or *Prevotella. intermedia* ATCC 25611, diluted to approximately $1 \times 10^6$ cfu (colony forming units) per mL, were added to the test wells in 100 µL quantities. Appropriate growth promotion and sterility controls were included. Plates were incubated at 37° C. anaerobically, until turbidity in the growth control well was observed. The MIC (minimum inhibitory concentration) was recorded as the lowest concentration inhibiting growth of the test organism as viewed with the unaided eye. *Streptococcus mutans* ATCC 25175 was tested in similar fashion, with Tryptic Soy Broth (TSB) as the test medium and incubation of plates at 37° C. with 5% $CO_2$. *Staphylococcus aureus* ATCC 6538 was tested using Tryptic Soy Broth (TSB) as the test medium and incubation of plates at 37° C. *Aspergillus niger* ATCC 16404 was tested, with Tryptic Soy Broth (TSB) as the test medium and incubated at room temperature (25° C.).

Results were recorded as the mode value from triplicate experiments vs. each bacterium. *P. intermedia* and *P. gingivalis* are gram negative bacteria involved in periodontitis. *Streptococcus mutans* is involved in caries formation. Both supercritical extracts were able to inhibit the growth of those 3 pathogenic bacteria at the lowest concentrations of extract tested. Supercritical licorice extracts of the present invention, with or without using or not ethanol as a modifier, were able to inhibit *P. intermedia* at a concentration of 12.5 μg/ml. The extract using ethanol as a modifier was able to inhibit the growth of *P. gingivalis* at the same level as chlorhexidine. The supercritical licorice extract of the present invention (with ethanol) was able to inhibit the growth of *S. mutans*, a cariogenic bacteria, at a concentration of 12.5 μg/ml. The supercritical licorice extract of the present invention without ethanol was only tested to 31.25 μg/ml. See, Table 1.

TABLE 1

Antibacterial activity against oral bacteria

|  | licorice $CO_2$—to extract (μg/ml) | licorice $CO_2$—EtOH extract (μg/ml) | Chlorhexidine |
|---|---|---|---|
| *Prevotella intermedia* | 12.5 | 12.5 | 3.125 |
| *Porphyromonas gingivalis* | 12.5 | 6.25 | 6.25 |
| *Streptococcus mutans* | <31.25* | 12.5 | 1.56 |

*The lowest concentration tested was 31.25 μg/ml

Biofilm formation and viability: A 24 h culture of *P. gingivalis* (ATCC 33277) in Todd-Hewitt broth supplemented with hemin and vitamin K (THB-HK) was diluted in fresh broth medium to obtain an optical density at 655 nm ($OD_{655}$) of 0.07. Samples (100 μL) were added to the wells of a 96-well tissue culture plate containing 100 μL of serial dilutions (0 to 500 μg/mL) of sterile plant extracts in THB-HK. Control wells with no extract were also inoculated. After incubation for 48 h at 37° C. under anaerobic conditions, spent media and free-floating bacteria were removed by aspiration using a 26 G needle and the wells were washed three times with distilled water. The *P. gingivalis* biofilms were stained with 0.4% crystal violet (100 μL) for 15 min. The wells were washed four times with distilled water to remove unbound crystal violet dye and dried for 2 h at 37° C. After adding 100 μL of 95% (v/v) ethanol to each well, the plate was shaken for 10 min to release the stain from the biofilms and the absorbance at 550 nm ($A_{550}$) was recorded. Assays were run in triplicate and the means±standard deviations of two independent experiments were calculated. See, Table 2.

The effect of plant fractions on *P. gingivalis* cell viability was investigated using the tetrazolium sodium 3'-{1-[(phenylamino)-carbonyl]-3,4-tetrazolium}-bis(4-methoxy-6-nitro) benzene sulfonic acid hydrate (XTT) reduction assay. Briefly, XTT was dissolved in PBS at 1 mg/mL and menadione was prepared in acetone at 1 mM. The XTT/menadione reagent contained 12.5 parts XTT/1 part menadione. A 48 h biofilm of *P. gingivalis* was prepared as above and treated with the plant fractions (0 to 250 μg/mL) for 2 h (anaerobiosis, 37° C.) prior to adding 25 μL XTT/menadione. After 1 h at 37° C., the absorbance at 490 nm ($A_{490}$) was read using a microplate reader. The licorice extract of the present invention was able to inhibit the growth of *P. gingivalis* and also inhibit the formation of *P. gingivalis*. *P. gingivalis* was then unable to attach (anti-adherence). When licorice extract was applied after the biofilm was formed, there was no desorption of the biofilm but the viability of the biofilm was reduced which means that the biofilm was not removed but that the bacteria forming the biofilm died. See, Table 2.

TABLE 2

Effect of licorice $CO_2$ extract biofilm formation, adherence properties and viability of *P. gingivalis*.

|  | Inhibit *P. gingivalis* biofilm. (anti-adherent) (μg/ml) | Desorption of *P. gingivalis* biofilm (μg/ml) | Growth of *P. gingivalis* (μg/ml) | Bactericide effect on *P. gingivalis* in a biofilm (cell viability) (μg/ml) |
|---|---|---|---|---|
| Licorice $CO_2$ Extract | 4.2 | — | 4.2 | 8 |

LPS preparations: *Aggregatibacter actinomycetemcomitans* ATCC 29522 (syns; *Actinobacillus actinomycetemcomitans*) and *P. gingivalis* ATCC 33277 were grown in their appropriate culture media. LPS were isolated from these bacterial strains by a method routinely used in our laboratory.

Treatments of macrophages: U937 cells (ATCC CRL-1593.2), a human monoblastic leukemia cell line, was cultivated at 37° C. in a 5% $CO_2$ atmosphere in RPMI-1640 supplemented with 10% FBS and 100 μg/mL of penicillin-streptomycin (RPMI-FBS). Monocytes ($2 \times 10^5$ cells/ml) were incubated in RPMI-10% FBS containing 10 ng/ml of phorbol myristic acid (PMA) for 48 h to induce differentiation into adherent macrophage-like cells. Following the PMA treatment, the medium was replaced with fresh medium and the differentiated cells were incubated for an additional 24 h prior to use. Adherent macrophages were suspended in RPMI-10% FBS and centrifuged at 200×g for 8 min. They were washed and suspended in RPMI-10% FBS at a density of $1 \times 10^6$ cells/ml and seeded in a 6 well-plate ($2 \times 10^6$ cells/well in 2 ml) at 37° C. in a 5% $CO_2$ atmosphere.

The macrophages were treated with the licorice extract at concentrations up to 250 μg/ml and incubated at 37° C. in 5% $CO_2$ for 2 h before stimulation with LPS at a final concentration of 1 μg/ml. After a 24 h incubation (37° C. in 5% $CO_2$), the culture medium supernatants were collected and stored at −20° C. until used. Cells incubated in culture medium with or without licorice extract, but not stimulated with LPS, were used as controls.

Determination of cytokine levels: Commercial enzyme-linked immunosorbent assay (ELISA) kits (R&D Systems, Minneapolis, Minn., U.S.A.) were used to quantify IL-1β, IL-6, IL-8, and TNF-α concentrations in the cell-free culture supernatants according to the manufacturer's protocols. The absorbance at 450 nm was read in a microplate reader with the wavelength correction set at 550 nm.

Statistical analysis: Two-way analyses of variance were performed to compare the means of the different conditions. Differences were considered significant at the 0.05 level (P value).

Anti-inflammatory effect. The extracts of the present invention caused a significant inhibition in vitro of interleukin 1β, interleukin 8 and tumor necrosis α production by macrophages produced from a U937 cells, a human monoblastic leukemia cell line stimulated with LPS of *Aggregatibacter actinomycetemcomitans* at a concentration of 10 μg/ml and at 5 μg/ml for interleukin 6. These results were confirmed in two independent experiments.

Licorice extract caused a significant inhibition in vitro of interleukin 6, interleukin 8 and tumor necrosis factor-α (TNF-α) production by macrophages stimulated with LPS of *P. gingivalis* at a concentration varying from 5-10 μg/ml. These results were confirmed in two independent experiments.

HPLC Analysis of the Supercritical $CO_2$ Extract

Samples of the extracts of the present invention and extracts produced by prior art methods were analyzed by high pressure liquid chromatography (HPLC). The specifications for the procedure used were as follows:

HPLC was performed on a Zorbax Eclipse XDB C-18 (Agilent Technologies, Santa Clara, Calif.) 250×4.6 mm i.d., 5 μm, with Zorbax C-18 Guard Column: (Cat. # HP 990967-902 and HP 820950-925).

| Mobile Phase: | MeCN (0.05% TFA)-H$_2$O (0.05% TFA) | |
|---|---|---|
| 0 min. | 45 | 55 |
| 3 min. | 45 | 55 |
| 25 min. | 100 | 0 |
| 25.1 min. | 45 | 55 |
| Conditioning: | at least 20 min. | |
| Flow Rate: | 1.0 ml/min | |
| Col. Temp: | 30° C. | |
| Detector: | 280 nm (bw 16, reference 450 nm, bw 100) | |
| Run time: | 25 min. | |
| Post time: | 5 min. | |

Figure 1:
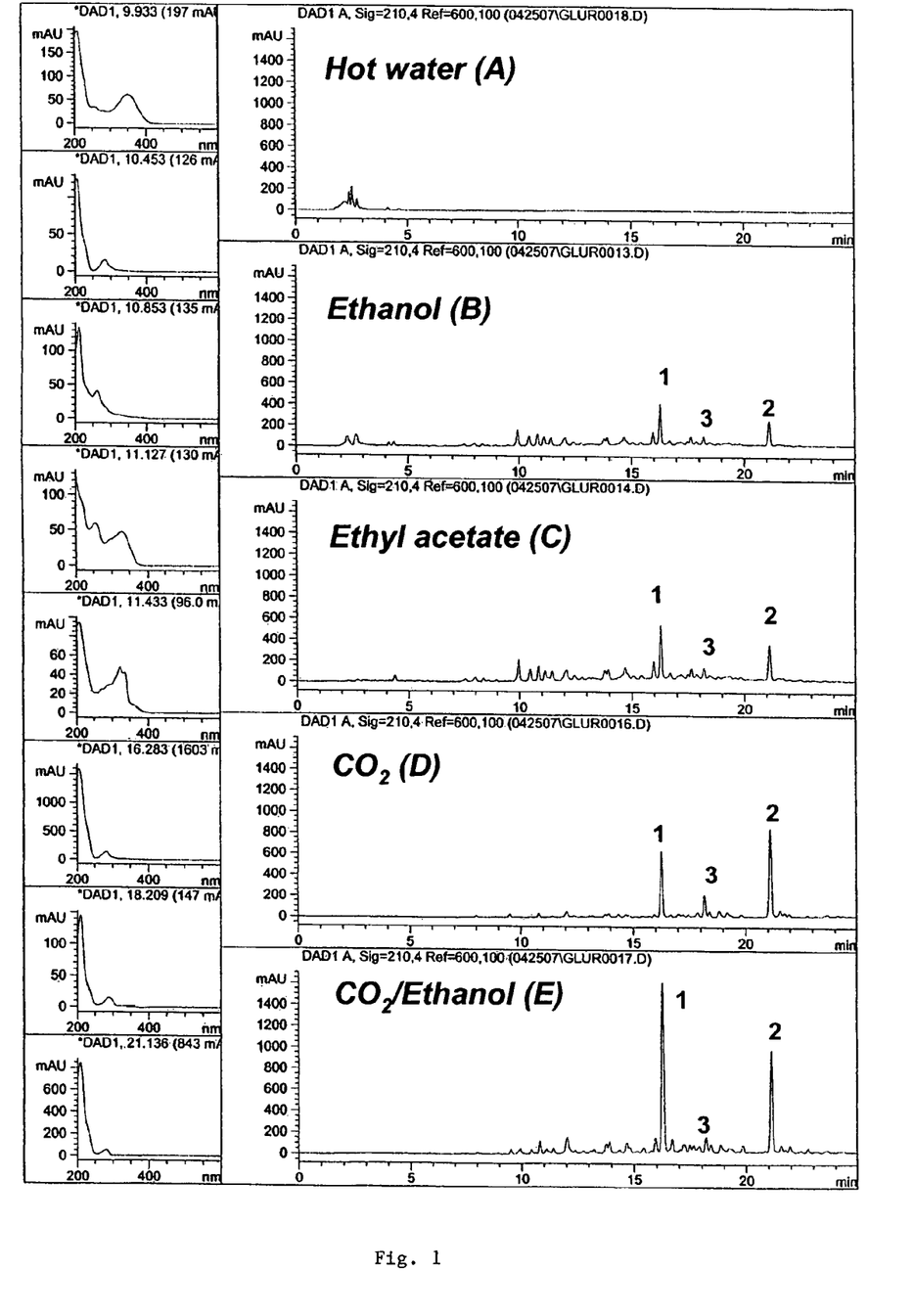
FIG. 1 shows a HPLC chromatogram of extracts of *Glycyrrhiza uralensis* generated with A) hot water extraction, B) ethanol extraction, C) ethyl acetate extraction, D) Supercritical CO$_2$ extraction and E) Supercritical CO$_2$ extraction with ethanol as a modifier.
Figure 2:
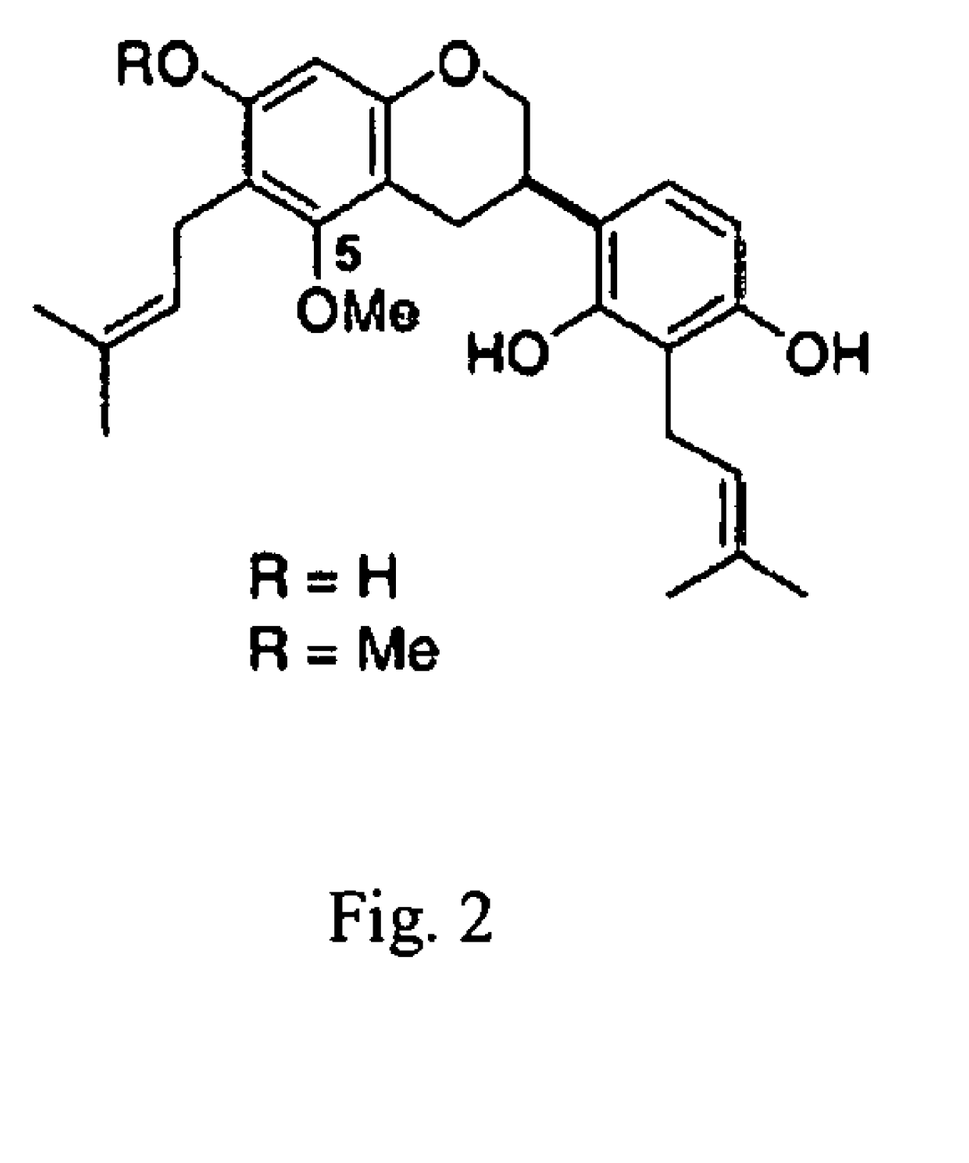
FIG. 2 shows the chemical structures of licoricidin and 5-O-methyllicoricidin wherein R=H for licoricidin and R=Me for 5-O-methyllicoricidin.

The results are presented in FIG. 1. The first chromatogram (A) shows an extract with hot water and it contains only hydrophilic compounds. The peak eluting after 4.5 min is glycyrrhizic acid. According to the UV spectrum and the retention time, glycyrrhizic acid is only present in the hot water extract. The second chromatogram (B) is a 100% ethanol extract and the chromatogram (C) is an ethyl acetate extract, both are very similar in composition, with the exception that B contains more hydrophilic compounds (eluting between 0-4 min.). The major components of the $CO_2$ extract are licoricidin (1, eluting after 16.5 min) and 5-O-methyllicoricidin (2, eluting after 21 min.), together with an unidentified flavonoid peak 3 around 18 min. The supercritical extract using ethanol (EtOH) as a modifier contains more hydrophilic compounds that the supercritical extract without modifier, and contains the highest amounts of licoricidin and 5-O-methyllicoricidin. Moreover, from an environmental point of view, the $CO_2$ extract uses only a small percentage of ethanol (5-10%) to achieve a good balance of hydrophilic and lipophilic compounds. In both supercritical extracts, the 5-O-methyllicoricidin and licoricidin are highly dominant.

We claim:

1. An oral care or body care composition comprising a supercritical $CO_2$ extract of the root of the plant *Glycyrrhiza* sp., wherein said extract comprises an antibacterial effective amount of a plurality of prenylated flavonoids; and
an orally acceptable carrier;
wherein said composition is substantially free of glycyrrhizic acid.

2. The oral care or body care composition of claim 1, wherein the plurality of prenylated flavonoids is at least two selected from the group consisting of: licoricidin; glabridin; methylglabridin; glabrol; and 5-O-methyllicoricidin.

3. The oral care composition of claim 1, wherein said oral care composition is selected from the group consisting of: a dentifrice a toothpaste, a denture cleaner, dental floss, a toothpick, mouthwash, mouth-rinse, a pastille, chewing gum, a dissolvable tablet, a chewable tablet and a lozenge.

4. The composition of claim 3, wherein said composition is a dentifrice; and wherein the plurality of prenylated flavonoids is present at a concentration of 0.002-2.0%, by weight.

5. The composition of claim 3, wherein said composition is a denture cleaner; and wherein the plurality of prenylated flavonoids is present at a concentration of 0.002-2.0%, by weight.

6. The composition of claim 3, wherein said composition is a mouthwash or mouthrinse; and wherein the plurality of prenylated flavonoids is present at a concentration of 0.002-1.0%, by weight.

7. The composition of claim 3, wherein said composition is a pastille, chewing gum, or a lozenge; and wherein the plurality of prenylated flavonoids is present at a concentration of 0.005-10.0%, by weight.

8. The composition of claim 3, wherein said composition is a dissolvable tablet; and wherein the plurality of prenylated flavonoids is present at a concentration of 0.01-5.0%, by weight.

9. The composition of claim 3, wherein said composition is dental floss; and wherein the plurality of prenylated flavonoids is present at a concentration of 0.1-5.0%, by weight, of the wax mixture used to coat or impregnate said dental floss.

10. The composition of claim 1 wherein the major components of said extract are licoricidin and 5-O-methyllicoricidin.

11. An oral care or body care composition comprising:
a supercritical $CO_2$ extract of the root of the plant *Glycyrrhiza* sp., wherein said extract comprises an anti-inflammatory effective amount of a plurality of prenylated flavonoids; and
an orally acceptable carrier;
wherein said composition is substantially free of glycyrrhizic acid.

12. The composition of claim 11, wherein the plurality of prenylated flavonoids is selected from the group consisting of: licoricidin; glabridin; methylglabridin; glabrol; and 5-O-methyllicoricidin.

13. The oral care composition of claim 11, wherein said composition is in a form selected from: a dentifrice a toothpaste; a denture cleaner; dental floss; a toothpick; mouthwash; mouth-rinse; a pastille; chewing gum; a dissolvable tablet; a chewable tablet; and a lozenge.

14. The composition of claim 13, wherein said composition is a dentifrice; and wherein the plurality of prenylated flavonoids is present at a concentration of 0.002-2.0%, by weight.

15. The composition of claim 13, wherein said composition is a denture cleaner; and wherein the plurality of prenylated flavonoids is present at a concentration of 0.002-2.0%, by weight.

16. The composition of claim 13, wherein said composition is a mouthwash or mouthrinse; and wherein the plurality of prenylated flavonoids is present at a concentration of 0.002-1.0%, by weight.

17. The composition of claim 13, wherein said composition is a pastille, chewing gum, or a lozenge; and wherein the plurality of prenylated flavonoids is present at a concentration of 0.005-10.0%, by weight.

18. The composition of claim 13, wherein said composition is a dissolvable tablet; and wherein the plurality of prenylated flavonoids is present at a concentration of 0.01-5.0%, by weight.

19. The composition of claim 13, wherein said composition is dental floss; and wherein the plurality of prenylated flavonoids is present at a concentration of 0.1-5.0%, by weight, of the wax mixture used to coat or impregnate said dental floss.

20. The composition of claim 11 wherein the major components of said extract are licoricidin and 5-O-methyllicoricidin.

* * * * *